United States Patent
Kang et al.

(10) Patent No.: US 11,969,232 B2
(45) Date of Patent: Apr. 30, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Jae Min Kang, Seoul (KR); Seung Woo Noh, Seongnam-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 310 days.

(21) Appl. No.: 17/237,888

(22) Filed: Apr. 22, 2021

(65) Prior Publication Data

US 2022/0117499 A1    Apr. 21, 2022

(30) Foreign Application Priority Data

Oct. 20, 2020 (KR) .......................... 10-2020-0135936

(51) Int. Cl.
| | | |
|---|---|---|
| *A61B 5/0205* | (2006.01) | |
| *A61B 5/02* | (2006.01) | |
| *A61B 5/021* | (2006.01) | |
| *A61B 5/026* | (2006.01) | |
| *A61B 5/1172* | (2016.01) | |
| *A61B 5/16* | (2006.01) | |

(52) U.S. Cl.
CPC ........ *A61B 5/0205* (2013.01); *A61B 5/02007* (2013.01); *A61B 5/02108* (2013.01); *A61B 5/0261* (2013.01); *A61B 5/1172* (2013.01); *A61B 5/165* (2013.01); *A61B 2562/0247* (2013.01)

(58) Field of Classification Search
CPC ............. A61B 5/0205; A61B 5/02007; A61B 5/02108; A61B 5/0261; A61B 5/1172; A61B 5/165; A61B 2562/0247; A61B 5/6843; A61B 5/02255; A61B 5/6826; A61B 5/6898
See application file for complete search history.

(56) References Cited

U.S. PATENT DOCUMENTS

| 9,867,513 B1 * | 1/2018 | Hall ........................ A47K 13/24 |
|---|---|---|
| 10,736,511 B2 | 8/2020 | Robinson et al. |
| 10,813,561 B2 | 10/2020 | Kwon et al. |

(Continued)

FOREIGN PATENT DOCUMENTS

| JP | 2016-55092 A | 4/2016 |
|---|---|---|
| JP | 2017-171078 A | 9/2017 |

(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for non-invasively estimating bio-information includes an image sensor configured to acquire a first contact image of an object, based on the object being in contact with the image sensor, an actuator, and a processor configured to determine a contact position and a direction of the object, based on the acquired first contact image, and control the actuator to adjust a position of the image sensor, based on the determined contact position and the determined direction of the object so that a field of view (FOV) of the image sensor moves to a predefined measurement area on the object.

18 Claims, 16 Drawing Sheets

(56) References Cited

U.S. PATENT DOCUMENTS

| | | | |
|---|---|---|---|
| 2007/0258628 A1* | 11/2007 | Schneider | A61B 5/1172 |
| | | | 73/620 |
| 2015/0366464 A1 | 12/2015 | Gu | |
| 2016/0198955 A1 | 7/2016 | Fortin | |
| 2017/0340209 A1 | 11/2017 | Klaassen et al. | |
| 2018/0338692 A1 | 11/2018 | Robinson et al. | |
| 2019/0239758 A1 | 8/2019 | Park et al. | |
| 2019/0290131 A1 | 9/2019 | Robinson et al. | |
| 2019/0328293 A1 | 10/2019 | Dang et al. | |
| 2020/0015689 A1 | 1/2020 | Allen et al. | |
| 2020/0297224 A1 | 9/2020 | Mori et al. | |
| 2020/0383590 A1 | 12/2020 | Robinson et al. | |

FOREIGN PATENT DOCUMENTS

| | | |
|---|---|---|
| JP | 2019-107250 A | 7/2019 |
| KR | 10-0660349 B1 | 12/2006 |
| KR | 10-2018-0076050 A | 7/2018 |
| KR | 10-2019-0073123 A | 6/2019 |
| KR | 10-2019-0084093 A | 7/2019 |
| KR | 10-2019-0094730 A | 8/2019 |

* cited by examiner

APPARATUS AND METHOD FOR ESTIMATING BIO-INFORMATION

CROSS-REFERENCE TO RELATED APPLICATION

This application claims priority under 35 U.S.C. § 119 to Korean Patent Application No. 10-2020-0135936, filed on Oct. 20, 2020, in the Korean Intellectual Property Office, the disclosure of which is incorporated by reference herein in its entirety.

BACKGROUND

1. Field

Apparatuses and methods consistent with example embodiments relate to non-invasively estimating bio-information.

2. Description of Related Art

Methods of non-invasively measuring blood pressure without damaging a human body include a method of measuring blood pressure by measuring a cuff-based pressure and a method of estimating blood pressure by measuring a pulse wave without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point at which a change in a pressure signal is large.

Cuffless blood pressure measurement methods may include a method of measuring blood pressure by calculating a pulse transit time (PTT) and a pulse wave analysis (PWA) method of estimating blood pressure by analyzing a shape of a pulse wave.

SUMMARY

In accordance with an aspect of an example embodiment, there is provided an apparatus for estimating bio-information including an image sensor configured to acquire a first contact image of an object, based on the object being in contact with the image sensor, an actuator, and a processor configured to determine a contact position and a direction of the object, based on the acquired first contact image, and control the actuator to adjust a position of the image sensor, based on the determined contact position and the determined direction of the object so that a field of view (FOV) of the image sensor moves to a predefined measurement area on the object.

The processor may be further configured to extract a characteristic point of the object, from the acquired first contact image, and determine the contact position and the direction, based on the extracted characteristic point.

The characteristic point of the object may include a fingerprint center point of a finger.

The processor may be further configured to determine whether the extracted characteristic point exists in the first contact image, and based on the extracted characteristic point being determined to not exist in the first contact image, guide a user to bring the object into contact with the image sensor.

The processor may be further configured to determine whether the extracted characteristic point exists in the first contact image, and based on the extracted characteristic point being determined to not exist in the first contact image, repeat a predetermined number of times of controlling the actuator to adjust the position of the image sensor to an arbitrary position and then extracting the characteristic point, from the acquired first contact image acquired after the position of the image sensor is adjusted.

The processor may be further configured to determine whether the extracted characteristic point exists in the first contact image, and based on the extracted characteristic point being determined to not exist in the first contact image, estimate a position of the characteristic point by comparing a reference contact image and the acquired first contact image.

The processor may be further configured to determine a displacement of the image sensor, based on the determined contact position and the determined direction, and control the actuator to adjust the position of the image sensor, based on the determined displacement.

The image sensor may be further configured to acquire a second contact image of the object, based on the position of the image sensor being adjusted, and the processor may be further configured to extract a pulse wave signal, based on a pixel intensity of the acquired second contact image, and estimate the bio-information, based on the extracted pulse wave signal.

The processor may be further configured to generate an oscillogram, based on the extracted pulse wave signal and a contact pressure of the object, and estimate the bio-information, based on the generated oscillogram.

The apparatus may further include a force/pressure sensor configured to measure a contact force or the contact pressure that is applied between the object and the image sensor, based on the object in contact with the image sensor changing a force.

The processor may be further configured to acquire the contact pressure, based on the pixel intensity of the acquired second contact image and using a predefined contact pressure conversion equation.

The bio-information may include any one or any combination of a blood pressure, a vascular age, an arterial stiffness, an aortic pressure waveform, a blood vessel elasticity, a stress index, and a degree of fatigue.

In accordance with an aspect of an example embodiment, there is provided a method of estimating bio-information, the method including acquiring, by an image sensor, a first contact image of an object, based on the object being in contact with the image sensor, determining, by a processor, a contact position and a direction of the object, based on the acquired first contact image, and controlling, by the processor, an actuator to adjust a position of the image sensor, based on the determined contact position and the determined direction of the object so that a field of view (FOV) of the image sensor moves to a predefined measurement area on the object.

The determining of the contact position and the direction may include extracting a characteristic point of the object, from the acquired first contact image, and determining the contact position and the direction, based on the extracted characteristic point.

The method may further include determining whether the extracted characteristic point exists in the first contact image, and based on the extracted characteristic point being determined to not exist in the first contact image, guiding a user to bring the object into contact with the image sensor.

The method may further include determining whether the extracted characteristic point exists in the first contact image, and based on the extracted characteristic point being determined to not exist in the first contact image, repeating a predetermined number of times of controlling the actuator to adjust the position of the image sensor to an arbitrary position and then extracting the characteristic point, from the acquired first contact image acquired after the position of the image sensor is adjusted.

The method may further include determining whether the extracted characteristic point exists in the first contact image, and based on the extracted characteristic point being determined to not exist in the first contact image, estimating a position of the characteristic point by comparing a reference contact image and the acquired first contact image.

The controlling of the actuator may include determining a displacement of the image sensor, based on the determined contact position and the determined direction, and controlling the actuator to adjust the position of the image sensor, based on the determined displacement.

The method may further include acquiring a second contact image of the object, based on the position of the image sensor being adjusted, extracting a pulse wave signal, based on a pixel intensity of the acquired second contact image, and estimating bio-information, based on the extracted pulse wave signal.

The estimating of the bio-information may include generating an oscillogram, based on the extracted pulse wave signal and a contact pressure of the object, and estimating the bio-information, based on the generated oscillogram.

BRIEF DESCRIPTION OF THE DRAWINGS

The above and other aspects, features, and advantages of embodiments of the disclosure will be more apparent from the following description taken in conjunction with the accompanying drawings, in which.

DETAILED DESCRIPTION

Figure 1:
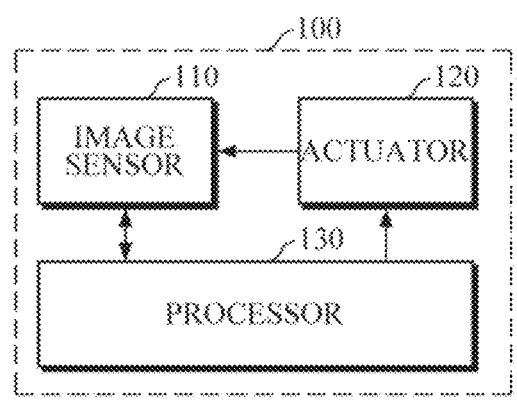
FIG. 1 is a block diagram illustrating an apparatus for estimating bio-information according to an example embodiment.

Details of example embodiments are provided in the following detailed description with reference to the accompanying drawings. The disclosure may be understood more readily by reference to the following detailed description of the example embodiments and the accompanying drawings. The disclosure may, however, be embodied in many different forms and may not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms first, second, etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, embodiments of an apparatus and method for estimating bio-information will be described in detail with reference to the drawings.

Embodiments of an apparatus for estimating bio-information described herein may be included in various information processing devices, such as a portable wearable device, a smart device, and the like. For example, various information processing devices may include various types of wearable devices, such as a smartwatch worn on a wrist, a smart band type wearable device, a headphone-type wearable device, and a hair band type wearable device, and mobile devices, such as a smartphone, a tablet personal computer (PC), etc. However, the information processing device is not limited to the above examples.

FIG. 1 is a block diagram illustrating an apparatus 100 for estimating bio-information according to an example embodiment.

Referring to FIG. 1, the bio-information estimation apparatus 100 includes an image sensor 110, an actuator 120, and a processor 130.

The image sensor 110 may optically acquire a contact image of an object. The image sensor 110 may include an optical-based image sensor, such as a CMOS Image Sensor (CIS), or a fingerprint sensor. However, aspects of the disclosure are not limited thereto, such that an array of, for example, photodiodes or photo transistors, may be formed, rather than the image sensor 110, a light signal detected from each pixel may be converted into an electrical signal, such as an electric charge or a voltage signal, and the electrical signal of each pixel may be output as pixel data.

The apparatus 100 for estimating bio-information may include a light source to emit light to the object when the object is in contact with the image sensor 110. The light source may include one or more light-emitting didoes (LEDs), laser diodes (LDs), phosphors, and the like, but is not limited thereto. Alternatively, instead of including a separate light source, light input from the outside may be used as a light source.

The actuator 120 may adjust a position of the image sensor 110 under the control of the processor 130. There is no particular limitation on the driving method of the actuator 120, such as a motor-based method, an encoder-based method, a piezo-based method, or the like. A maximum field of measurement (hereinafter referred to as "FOM") in which the actuator 120 can move the image sensor 110 to perform measurement may be preset and be stored in a memory.

The processor 130 may drive the actuator 120 on the basis of the contact image of the object acquired by the image sensor 110. The processor 130 may determine a current contact position and a current direction of the object by analyzing the contact image of the object. Also, when the current contact position and direction of the object is determined, the processor 130 may control the actuator 120 to move to a field of view (hereinafter referred to as "FOV") currently indicated by the image sensor 110 to a predefined desired measurement area on the object, on the basis of the determined current contact position and direction.

For example, the processor 130 may extract a characteristic point of the object from the contact image of the object and determine the current position and direction of the object based on the extracted characteristic point. For example, the processor 130 may determine the current position and direction by comparing the characteristic point of the object and a center point of a current FOV of the image sensor 110. In this case, when the object is a finger, the characteristic point may include a center point of a fingerprint of the finger. However, aspects of the disclosure are not limited thereto, and the object may be, for example, a predefined position of a blood vessel on the object. Even for the same object, the position of a blood vessel may be slightly different according to characteristics of each user, and thus can be acquired in advance for each user through a preprocessing process.

The processor 130 may calculate a displacement by which to move the image sensor 110 on the basis of the determined current contact position and direction of the object and control the image sensor 110 to acquire a contact image from a new position, i.e., the desired measurement area by driving the actuator according to the calculated displacement.

If the characteristic point does not exist in the contact image of the object, the processor 130 may guide the user to bring the object again into contact with the image sensor 110.

Also, when no characteristic point exists in the contact image of the object, the processor 130 may drive the actuator 120 to move the image sensor 110 to an arbitrary position for a predefined number of times instead of guiding the user to immediately re-contact, and may repeat the operation of extracting a characteristic point from a position adjusted by the image sensor 110 on the basis of the acquired contact image. When a characteristic point is not extracted even after a predetermined number of repetitions as described above, the processor 130 may guide the user to bring the object again into contact with the image sensor 110. In this case, the processor 130 may determine the arbitrary position to which the image sensor is to be moved by taking into account a relative position of the current FOV in the range of the FOM of the actuator.

In addition, when no characteristic point exists in the contact image of the object, the processor 130 may estimate a position of a characteristic point by comparing the contact image and a reference contact image, and move the FOV of the image sensor 110 to the estimated position of a characteristic point. In this case, the reference contact image may be a contact image acquired in a state in which the FOV of the image sensor 110 matches a measurement position of an object predefined for each use during the process of calibration. For example, a fingerprint image measured in advance from a user's finger may be set as a reference fingerprint image, and the position of a characteristic point may be estimated by comparing fingerprint patterns of a currently measured fingerprint image of the finger and the reference fingerprint image. At this time, the reference fingerprint image may be stored in a storage.

When the contact image is acquired in the desired measurement area of the object by driving the actuator, the processor 130 may estimate bio-information based on pixel data of the contact image. In this case, the bio-information may include blood pressure, vascular age, arterial stiffness, aortic pressure waveform, blood vessel elasticity, stress index, and a degree of fatigue, but is not limited thereto. Hereinafter, for convenience of description, blood pressure will be taken as an example.

When it is determined that the current FOV of the image sensor 110 matches the desired measurement area of the object, the processor 130 may estimate bio-information on the basis of the acquired current contact image without driving the actuator 120. For example, when a distance between the center point of the current FOV of the image sensor 110 and a fingerprint characteristic point is less than or equal to a predetermined threshold, it may be determined that the current FOV matches the desired measurement area of the object.

The processor 130 may extract a pulse wave signal on the basis of pixel data of the image sensor 110, i.e., the intensity of light received by each pixel while the object in contact with the image sensor 110 changes a contact pressure for a predetermined period of time, and may estimate blood pressure on the basis of the extracted pulse wave signal. In this case, the image sensor 110 may define an electrical signal value of each pixel as the intensity of each pixel. The intensity of each pixel may vary depending on the time for which the object is in contact with the image sensor 110, the area in which the object is in contact with the image sensor 110, or the like. For example, when the user brings his/her finger into contact with the image sensor 110 and gradually increases the pressing force for a predetermined period of time, the contact time and the contact area gradually increase and the intensity of each pixel increases. Hence, it can be seen that there is a correlation between the intensity of each pixel and the amplitude of the pulse wave signal.

For example, the processor 130 may convert the intensity of each pixel at each point in time into an amplitude value of a pulse wave signal at that point in time using a predefined amplitude conversion equation. The amplitude conversion equation may be a function equation that outputs any one of an average, a median, a minimum value, and a maximum value of pixel intensities as an amplitude value. However, aspects of the disclosure are not limited thereto, and the amplitude conversion equation may be defined as various liner or non-linear function equations.

The processor 130 may extract a feature related to blood pressure through, for example, an analysis of a waveform of a pulse wave signal, and estimate blood pressure using a predefined blood pressure estimation model. In this case, the feature may include time and/or amplitude of a maximum point of an amplitude of a pulse wave signal, a propagation wave constituting a pulse wave signal, time and/or amplitude of a pulse waveform related to a reflection wave, area information of a waveform of a pulse wave signal, and the like.

In another example, an oscillogram may be generated as described below, and blood pressure may be estimated by using the generated oscillogram. In this case, the processor 130 may convert the intensity of each pixel into a contact pressure by using a predefined contact pressure conversion equation. That is, as described above, as the contact pressure increases, the contact area increases and thus the intensity of each pixel increases. Accordingly, it can be seen that there is a correlation between the contact pressure and the intensity of each pixel. As described above, the contact pressure conversion equation that defines a correlation between the contact pressure and the intensity of each pixel may be predefined.

Figure 2:
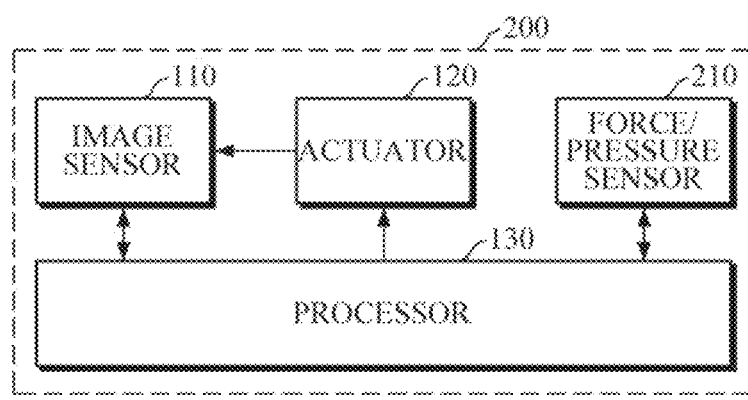
FIG. 2 is a block diagram illustrating an apparatus for estimating bio-information according to another example embodiment.

FIG. 2 is a block diagram illustrating an apparatus 200 for estimating bio-information according to another example embodiment.

Referring to FIG. 2, the apparatus 200 for estimating bio-information may include an image sensor 110, an actuator 120, a processor 130, and a force/pressure sensor 210. The image sensor 110, the actuator 120, and the processor 130 are described above, and hence detailed descriptions thereof will not be reiterated.

The force/pressure sensor 210 may be disposed on a lower portion of the image sensor 110 and measure a contact force or a contact pressure applied by an object to the image sensor 110. The force/pressure sensor 210 may include a single force sensor, such as a strain gauge, a force sensor array, a combination of a force sensor and an area sensor, or a pressure sensor. For example, the force sensor 210 may be a voltage resistance type force sensor, an ultrasonic type force sensor, a load cell sensor, a capacitive force sensor, a pyroelectric force sensor, a strain gauge type force sensor, an electrochemical force sensor, an optical force sensor, or a magnetic type force sensor.

When the contact force or contact pressure between the object and the image sensor 110 is acquired through the force/pressure sensor 210, the processor 130 may estimate blood pressure through oscillometry on the basis of a pulse wave signal extracted based on the contact force or contact pressure and the pixel intensity of the image sensor 110. In this case, when the contact force is measured, the contact force may be converted into a contact pressure based on the area of the image sensor 110.

Figure 3:
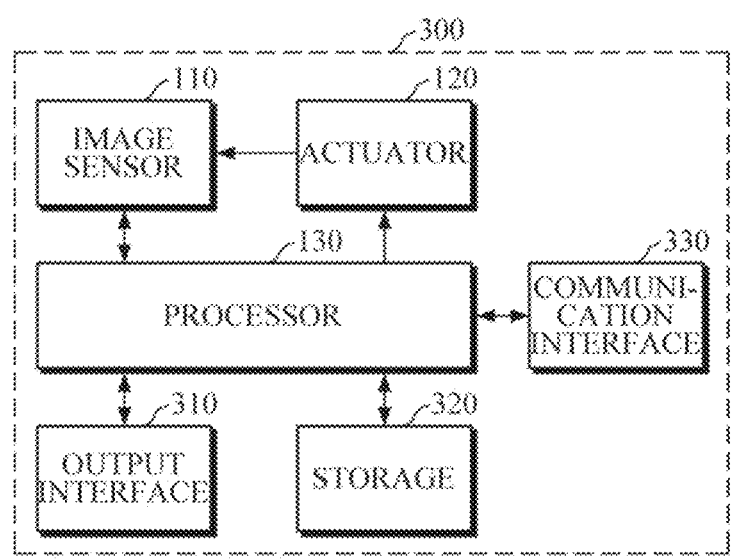
FIG. 3 is a block diagram illustrating an apparatus for estimating bio-information according to still another example embodiment.

FIG. 3 is a block diagram illustrating an apparatus 300 for estimating bio-information according to another example embodiment.

Referring to FIG. 3, the apparatus 300 for estimating bio-information may include an image sensor 110, an actuator 120, a processor 130, an output interface 310, a storage 320, and a communication interface 330. The apparatus 300 may further include a force/pressure sensor 210. The image sensor 110, the actuator 120, and the processor 130 are described above, and hence detailed descriptions thereof will not be reiterated.

The output interface 310 may provide a user with data generated during the process of estimating blood pressure by the processor 130. For example, the output interface 310 may display a contact image of an object or a blood pressure estimation result on a display. In this case, when an estimated blood pressure value is out of a normal range, warning information may be provided to the user by adjusting color or thickness of a line so that the user can easily recognize it or by being displayed together with the normal range. In addition, the output interface 310 may provide information related to the estimated blood pressure value to the user through a voice output interface, a haptic interface, or the like, together with or independently of a visual display, in a non-visual method, such as voice, vibration, tactile sensation, etc.

The storage 320 may store data related to the blood pressure estimation. For example, the storage 320 may store the contact image acquired through the image sensor 110, pixel data, various data generated in the blood pressure estimation process by the processor 130, for example, an extracted characteristic point, an estimated blood pressure value, or the like. Also, the storage 320 may store reference information, such as a blood pressure estimation model related to the blood pressure estimation, a contact pressure conversion equation, an amplitude conversion equation, or the like.

The storage 320 include at least one type of storage medium, such as a flash memory type, a hard disk type, a multimedia card micro type, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like, but is not limited thereto.

The communication interface 330 may communicate with an external device to transmit and receive various types of data related to the blood pressure estimation. The external device may include an information processing device, such as a smartphone, a tablet PC, a desktop PC, a laptop PC, and the like. For example, a blood pressure estimation result may be transmitted to the external device, such as a user's smartphone, so that the user can manage and monitor a component analysis result through a device which has a relatively high performance. In addition, information, such as a blood pressure estimation model, reference blood pressure, and the like, may be received from the external device and be stored in the storage 320.

The communication interface 330 may communicate with the external device by using various wired or wireless communication techniques including Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, the communication techniques are not limited thereto.

FIGS. 4A, 4B, 4C, 4D, 4E, 4F, 4G and 4H are diagrams for describing a structure of a sensor 41 and an example of image sensor position adjustment.

Example embodiments of a structure of the sensor and image sensor position adjustment will be described with reference to FIGS. 1 and 4A to 4H.

Figure 4A:
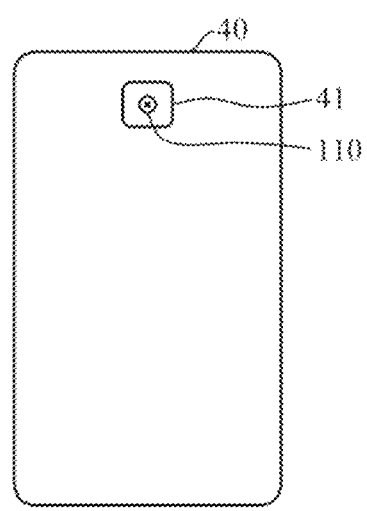
FIGS. 4A, 4B, 4C, 4D, 4E, 4F, 4G and 4H are diagrams for describing a structure of a sensor and image sensor position adjustment.

FIG. 4A illustrates a smart device 40 as one example of devices equipped with the apparatus 100 for estimating bio-information. As illustrated, the image sensor 110 of the apparatus 100 for estimating bio-information may be mounted in the sensor 41 on the rear surface of the smart device 40. However, aspects of the disclosure are not limited thereto, and a fingerprint sensor on the front surface for performing fingerprint authentication or a front-surface image sensor on may perform the function of the image sensor 110.

In the sensor 41, a filter array including a color filter for passing or blocking light of a wavelength range t may be arranged above each pixel of the image sensor 110. In addition, a lens for gathering light scattered, reflected, or transmitted from the object and directing the light to the image sensor 110 may be disposed in the sensor 41. Also, a micro lens for increasing the light-gathering ability may be disposed above each pixel of the image sensor 110. In this case, light emitted from the surrounding environment of the smart device 40 may be used as an external light source. Alternatively, a separate internal light source may be mounted around or inside the sensor 41 on the rear surface of the smart device 40.

Figure 4B:
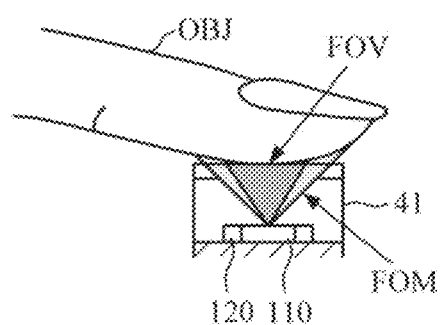

FIG. 4B illustrates a structure in which the image sensor 110 is disposed in the sensor 41 and the actuator 120 for adjusting a position of the image sensor 110 is disposed around the image sensor 110. As illustrated, the FOV of the image sensor 110 may be configured to be movable within the FOM according to the driving of the actuator 120.

Figure 4C:
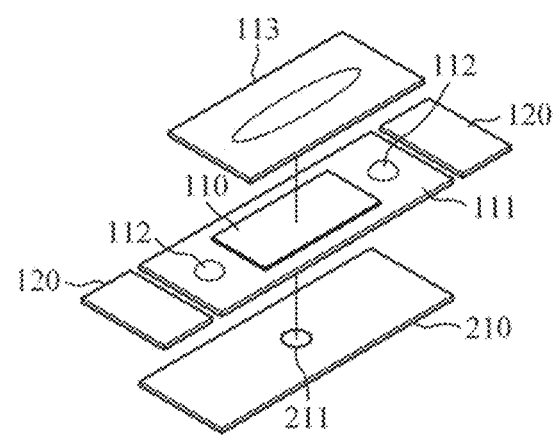
Figure 4D:
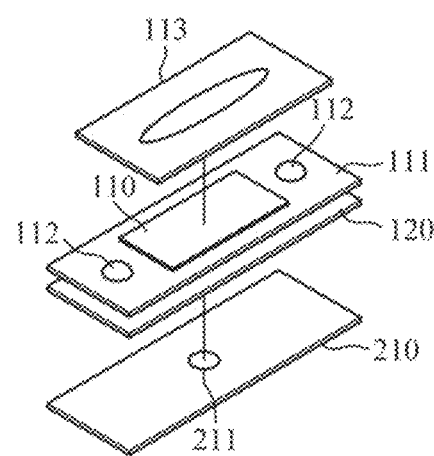
Figure 4E:
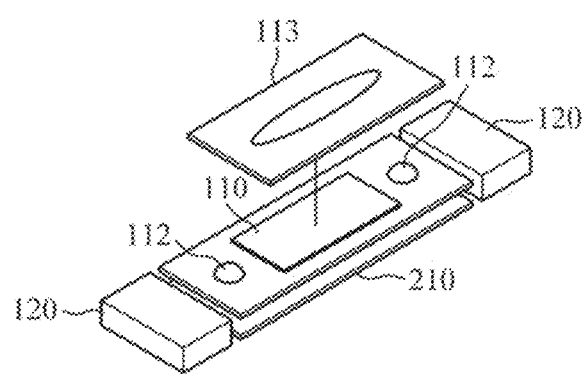

FIGS. 4C to 4E schematically illustrate structures for describing an arrangement relationship between the components of the sensor 41. However, aspects of the disclosure are not limited to the examples illustrated herein, and the structures may be variously changed according to the size, shape, or the like of a form factor. Referring to FIG. 4C, a lens 113 for gathering light from the object is disposed at an upper side, and an optical part 111 in which the image sensor 110 and one or more light sources 112 are disposed may be positioned at a lower side thereof. In this case, the actuator 120 may be disposed around the optical part 111 and adjust a position of the optical part 111, thereby adjusting a position of the image sensor 110. Also, the force sensor 210 may be disposed at a lower side of the optical part 111. The force sensor 210 may include, for example, a load cell 211. Referring to FIG. 4D, the lens 113 for gathering light from the object may be disposed at an upper side, and the optical part 111 may be disposed at a lower side thereof. In this case, the actuator 120 may be disposed at a lower side of the optical part 111 and adjust a position of the optical part 111. The force sensor 210 may be disposed at a lower side of the actuator 120. Referring to FIG. 4E, the lens 113, the optical part 111, and the force sensor 210 may be vertically disposed. In this case, the actuator 120 may be disposed on a side surface of the optical part 111 and the force sensor 210 and simultaneously move the positions of the optical part 111 and the force sensor 210.

Examples of adjusting the position of the image sensor will be described with reference to FIGS. 4F to 4H.

Figure 4F:
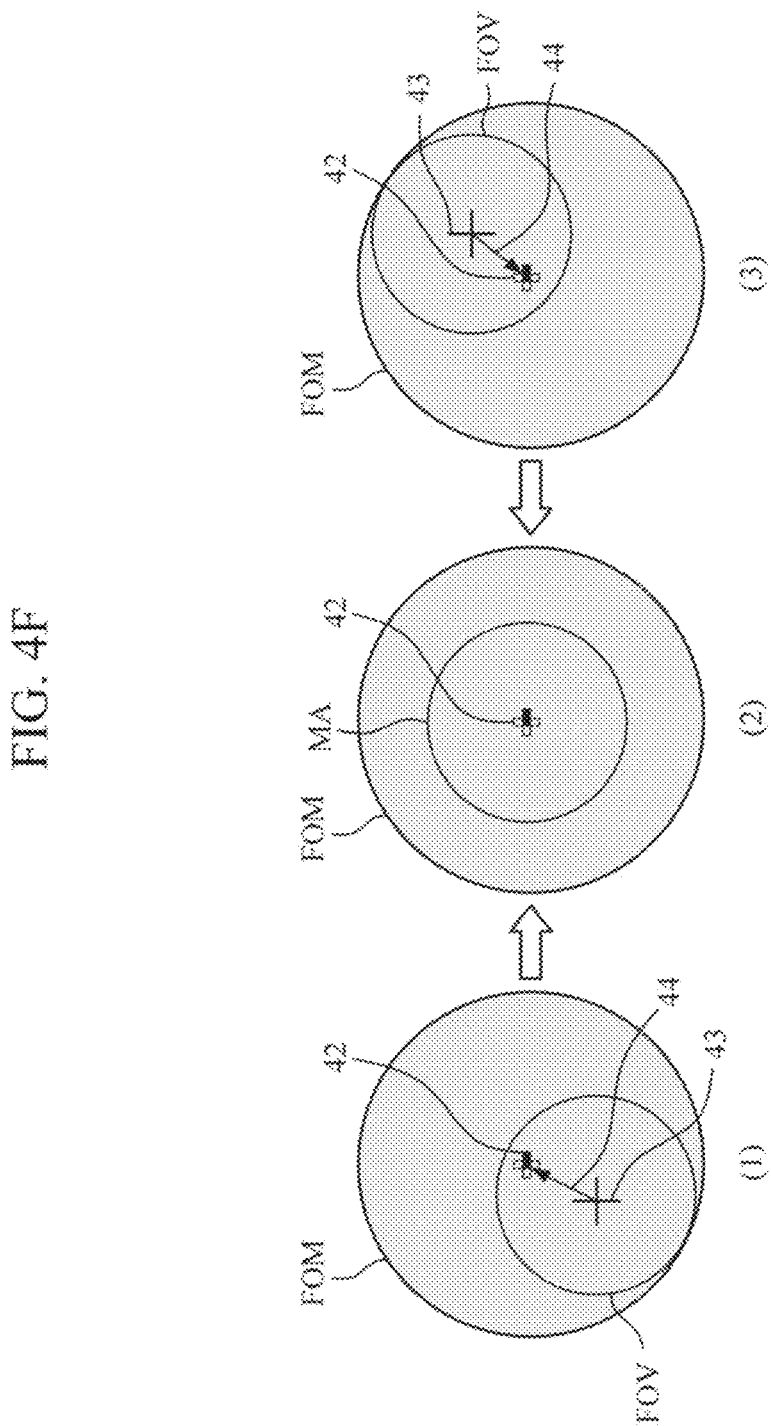

Referring to FIG. 4F, portion (1) illustrates that a finger is accurately in contact with the FOM of the image sensor 110, but the FOV of the image sensor 110 is skewed to the lower left side of the FOM so that a fingerprint image is acquired from the left lower side of a finger. The processor 130 may extract a characteristic point, for example, a fingerprint center point 42, from the fingerprint image in the current FOV. In addition, the processor 130 may compare a center point 43 of the FOV and the extracted fingerprint center point 42 and determine that a position of the object in currently contact with the image sensor 110 is in the lower left of the finger. When the contact position and direction are determined in this way, the processor 130 may calculate a displacement 44 by which to move the FOV of the image sensor 110, and control the actuator 120 by using the calculated displacement. In this case, the displacement may include information on a direction in which to move and a distance to move, and the displacement may be calculated so that the center of the FOV of the image sensor 110 matches the fingerprint center point.

Portion (2) of FIG. 4F illustrates that the FOV of the image sensor 110 is moved and matches a desired measurement area MA of the object as the processor 130 drives the actuator 120 as described above. In addition, portion (3) of FIG. 4F illustrates that the finger is accurately in contact with the FOM of the image sensor 110, but the FOV of the image sensor 110 is skewed to the upper right side of the FOM so that a fingerprint image is acquired from the upper right side of the finger. Likewise, the processor 130 may compare the extracted fingerprint center point 42 and the center point 43 of the FOV to calculate a displacement 44, and drive the actuator 120 according to the calculated displacement 44, thereby allowing the FOV to match the desired measurement area MA as shown in portion (2).

Figure 4G:
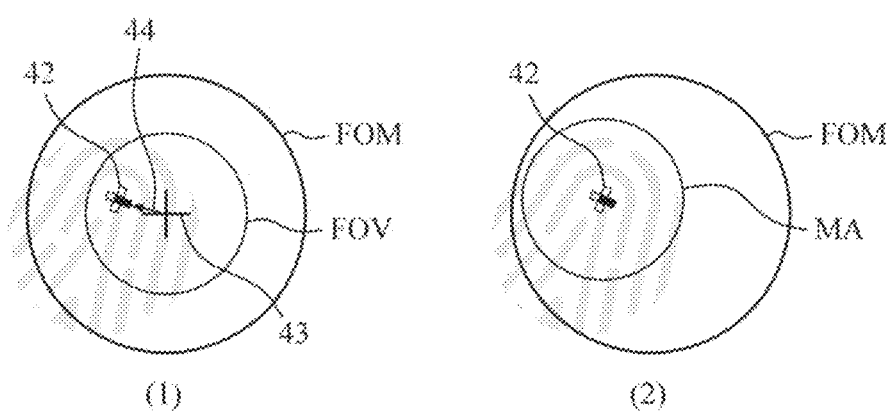

FIG. 4G illustrates that the fingerprint center point does not exist within the FOV of the image sensor 110 in a case in which a contact position of the finger is not appropriate and is thus skewed toward the side of the FOM of the image sensor 110. The processor 130 may extract a fingerprint center point 42 from a fingerprint image within the current FOV. Because the fingerprint center point 42 exists within the current FOV, the processor 130 may compare the extracted fingerprint center point 42 and the center point 43 of the FOV and determine that the current measurement area is in the right side of the finger. When the contact position and direction are determined in this way, the processor 130 may calculate a displacement 44 and control the actuator 120 by using the calculated displacement 44, thereby allowing the FOV to match the desired measurement area MA of the finger as shown in portion (2).

According to the disclosed embodiments, the FOV of the image sensor 110 is moved via the actuator 120 regardless of whether the contact position of the finger accurately contacts the FOM of the image sensor 110, and a signal is measured at the desired measurement area of the object, thereby improving the accuracy of bio-information estimation.

Figure 4H:
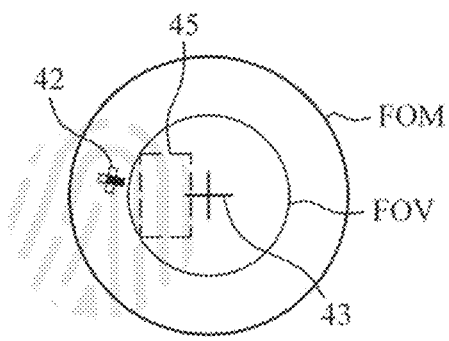

FIG. 4H illustrates that the fingerprint center point does not exist in the FOV of the image sensor 110 due to the improper contact position of the finger and thus skewed toward the side of the FOM of the image sensor 110. The processor 130 may guide the user to bring the finger again into contact with the image sensor 110 when the fingerprint center point 42 does not exist in the FOV. Alternatively, the processor 130 may repeat the process of extracting the fingerprint center point 42 by moving the FOV to an arbitrary position a predefined number of times.

For example, the processor 130 may analyze a fingerprint pattern from the contact image within the FOV and determine the arbitrary position to which to move the FOV. For example, because a fingerprint pattern located only on the left side of the center point 43 of the FOV as illustrated, it may be assumed that the fingerprint center point is positioned further left, and the FOV may be moved by a predetermined displacement in the left direction. Alternatively, a partial fingerprint image 45 partially overlapping the FOV may be compared with the reference fingerprint image to estimate a portion of the reference image which corresponds to the partial fingerprint image, a position of the fingerprint center point 42 may be estimated according to the estimation result and a direction of movement may be determined.

Figure 5A:
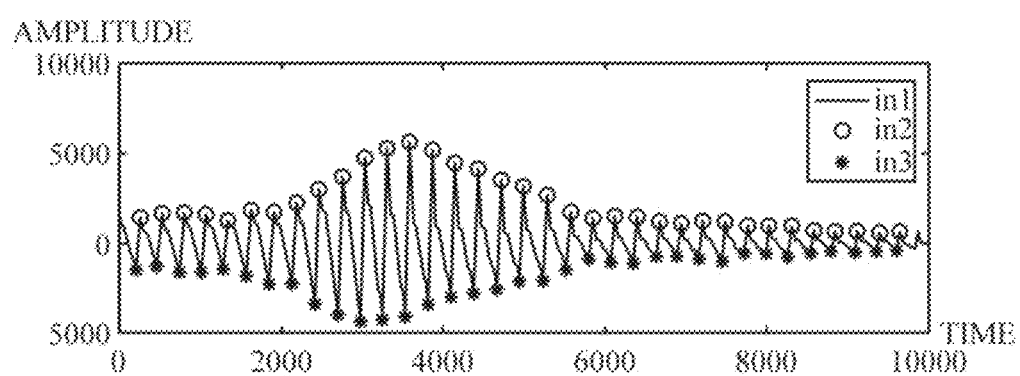
FIGS. 5A and 5B are graphs for describing oscillometric-based blood pressure estimation.
Figure 5B:
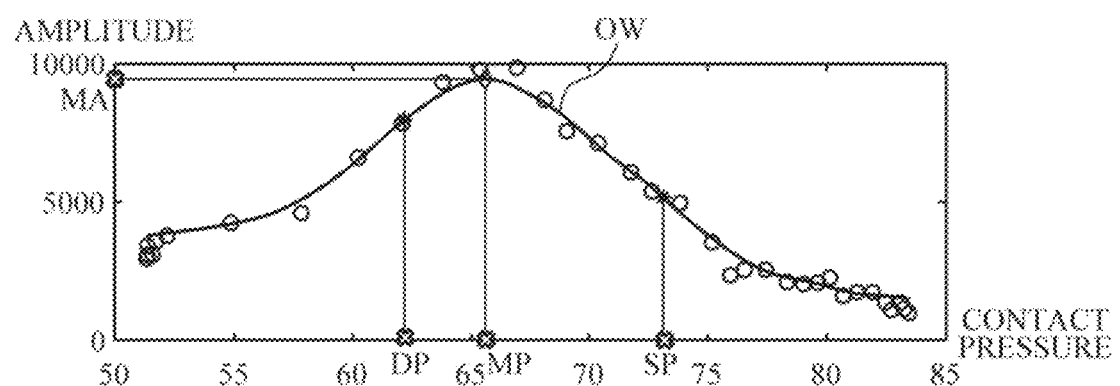

FIGS. 5A and 5B are graphs for describing an example of oscillometric-based blood pressure estimation. FIG. 5A shows a change in amplitude of a pulse wave signal while the object in contact with the image sensor 110 gradually increases pressure. FIG. 5B shows an oscillogram OW showing a relationship between the change in contact pressure and the amplitude of the pulse wave signal.

The processor 130 may extract a peak-to-peak point by, for example, subtracting an amplitude value in3 of a negative (−) point of a pulse wave signal waveform envelope in1 from an amplitude value in2 of a positive (+) point at each measurement time point. In addition, an oscillogram OW may be obtained by plotting a peak-to-peak amplitude based on a contact pressure value at the corresponding time point and performing, for example, polynomial curve fitting.

The processor 130 may estimate blood pressure using the oscillogram OW generated as described above. For example, mean arterial pressure (MAP) may be estimated based on a contact pressure MP at a pulse wave maximum point MA in the oscillogram. For example, the contact pressure MP at the pulse wave maximum point MA may be determined as MAP. Alternatively, the MAP may be estimated by applying the contact pressure to a predefined MAP estimation equation. In this case, the MAP estimation equation may be defined as various linear or non-linear combination functions, such as addition, subtraction, division, multiplication, logarithmic value, regression equation, and the like, with no specific limitation.

In addition, the processor 130 may estimate diastolic blood pressure and systolic blood pressure based, respectively, on contact pressure values DP and SP at points on the left and right of the pulse wave maximum point MA, at each of which an amplitude has a value equal to a predetermined ratio (e.g., 0.5 to 0.7) to the amplitude value at the pulse wave maximum point MA. Likewise, the contact pressures DP and SP may be determined as diastolic blood pressure and systolic blood pressure, respectively, and the diastolic blood pressure and the systolic blood pressure may be estimated using a predefined diastolic blood pressure estimation equation and a predefined systolic blood pressure estimation equation.

Figure 6:
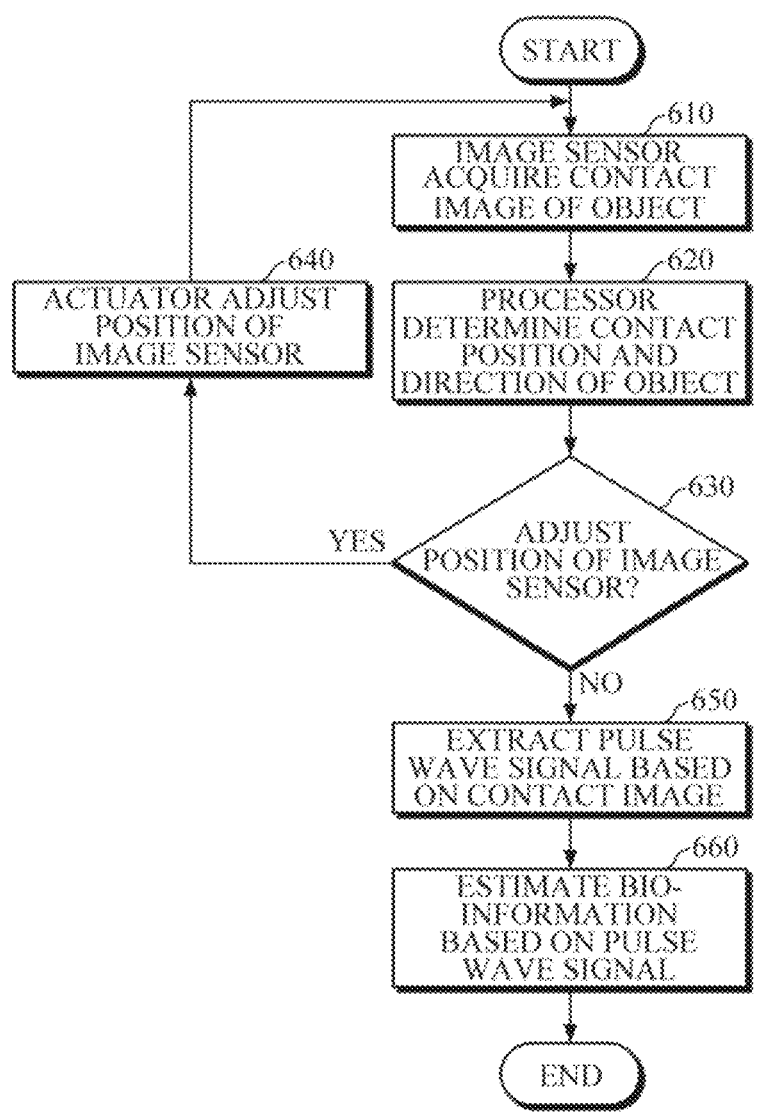
FIG. 6 is a flowchart illustrating a method of estimating bio-information according to an example embodiment.

FIG. 6 is a flowchart illustrating a method of estimating bio-information according to an example embodiment.

The method of FIG. 6 may correspond to one embodiment of method performed by the apparatuses 100, 200, 300 for estimating bio-information according to the embodiments of FIGS. 1 to 3. The method is described in detail above, and hence will be briefly described hereinafter.

In operation 610, when an object is in contact with the image sensor, the image sensor may acquire a contact image of the object.

In operation 620, the processor may determine a contact position and direction of the object on the basis of the contact image of the object acquired in operation 610. For example, the processor may extract a characteristic point of the object from the contact image and determine the current position and direction of the object based on the extracted characteristic point. For example, the processor may determine the current position and direction by comparing the characteristic point of the object and a center point of a current FOV of the image sensor.

In operation 630, based on the determined contact position and direction, it may be determined whether a position of the image sensor is to be adjusted. For example, if a distance between the center point of the current FOV of the image sensor and a fingerprint characteristic point is less than a predetermined threshold, it may be determined that the current FOV matches the desired measurement area of the object, and otherwise, it may be determined that the position of the image sensor is to be adjusted.

When it is determined in operation 630 that the position of the image sensor is to be adjusted, in operation 640, an actuator is driven to adjust the position of the image sensor, and the flowchart returns to operation 610 to acquire a contact image of the object at the adjusted position. In this case, a displacement of the image sensor may be calculated based on the characteristic point of the object and the actuator may be driven based on the calculated displacement.

When it is determined in operation 630 that the position of the image sensor is not to be adjusted, in operation 650, a pulse wave signal may be extracted based on the contact image acquired in operation 610. For example, an amplitude value of a pulse wave signal may be acquired based on the intensity of light received by each pixel of the image sensor for a predetermined period of time.

In operation 660, bio-information may be estimated based on the extracted pulse wave signal. For example, blood pressure may be estimated through oscillometry on the basis of the pulse wave signal and a contact pressure. In this case, the contact pressure may be measured by a force/pressure sensor, or may be acquired through conversion based on the intensity of light received by each pixel of the image sensor. An estimated bio-information value acquired as described above may be output to a user.

Figure 7:
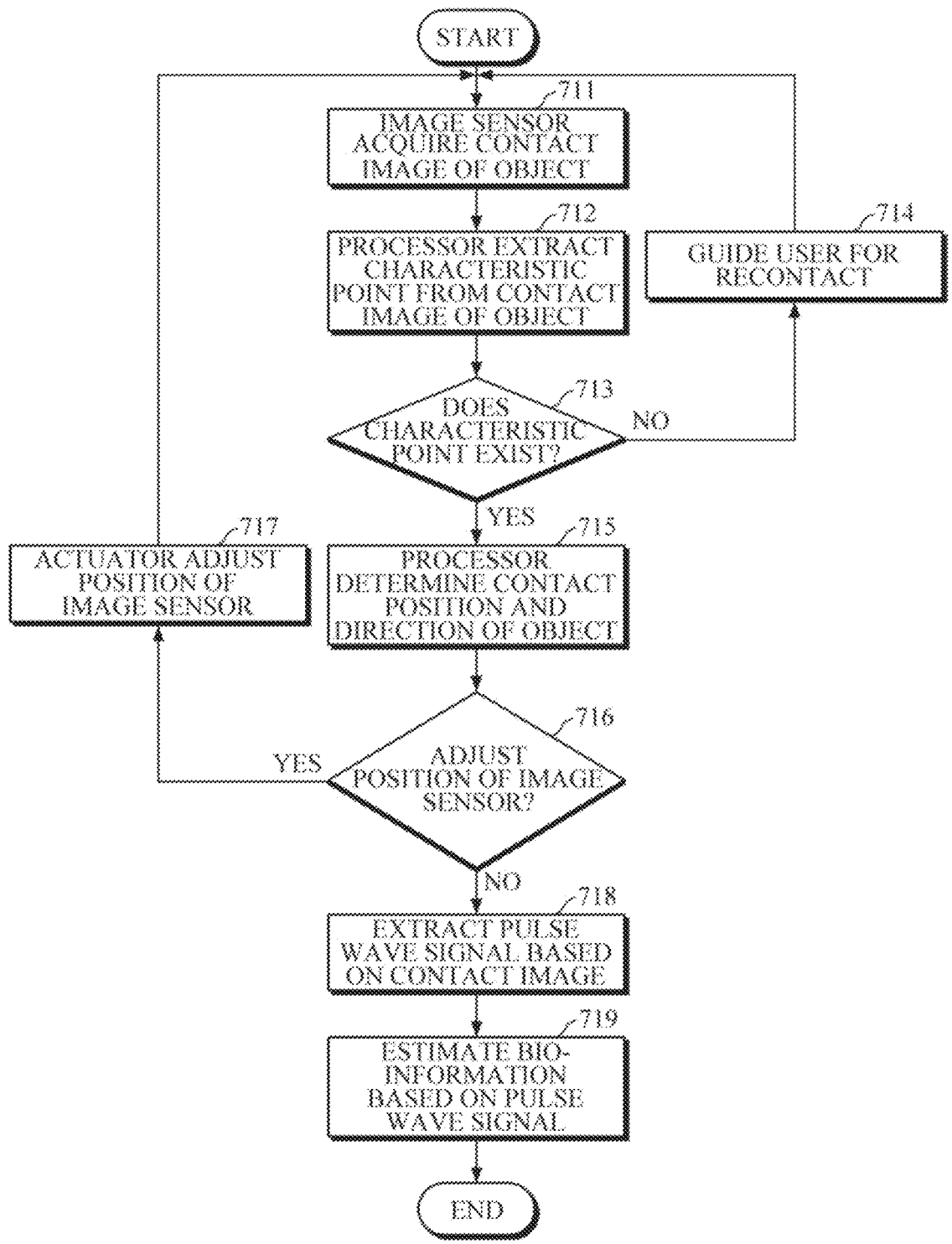
FIG. 7 is a flowchart illustrating a method of estimating bio-information according to another example embodiment.

FIG. 7 is a flowchart illustrating a method of estimating bio-information according to an example embodiment.

The method of FIG. 7 may correspond to another embodiment of the method performed by the apparatuses 100, 200, and 300 for estimating bio-information according to the embodiments of FIGS. 1 to 3. The method is described in detail above, and hence will be briefly described hereinafter.

In operation 711, when an object is in contact with the image sensor, the image sensor may acquire a contact image of the object.

In operation 712, the processor may extract a characteristic point from the acquired contact image of the object. In this case, the characteristic point is a reference point within a desired measurement area of the object and may include, for example, a center point of a fingerprint or a position of a predetermined blood vessel within the measurement area.

When the characteristic point is not extracted in operation 712, that is, when the characteristic point does not exist in the FOV of the image sensor (operation 713—No), in operation 714, a user may be guided for recontact. When the characteristic point is extracted in operation 712 (operation 713—Yes), in operation 715, the contact position and direction of the object may be determined based on the extracted characteristic point. In this case, the contact position and direction may be determined based on the extracted characteristic point and the center point of the FOV of the image sensor.

In operation 716, based on the determined contact position and direction, it is determined whether the position of the image sensor is to be adjusted.

When the position of the image sensor is to be adjusted, in operation 717, the position of the image sensor may be adjusted by driving the actuator. In this case, a displacement of the image sensor may be calculated based on the characteristic point of the object and the actuator may be driven based on the calculated displacement.

When it is determined in operation 716 that the position of the image sensor is not to be adjusted, in operation 718, a pulse wave signal may be extracted based on the contact image, and in operation 719, bio-information may be estimated based on the extracted pulse wave signal.

Figure 8:
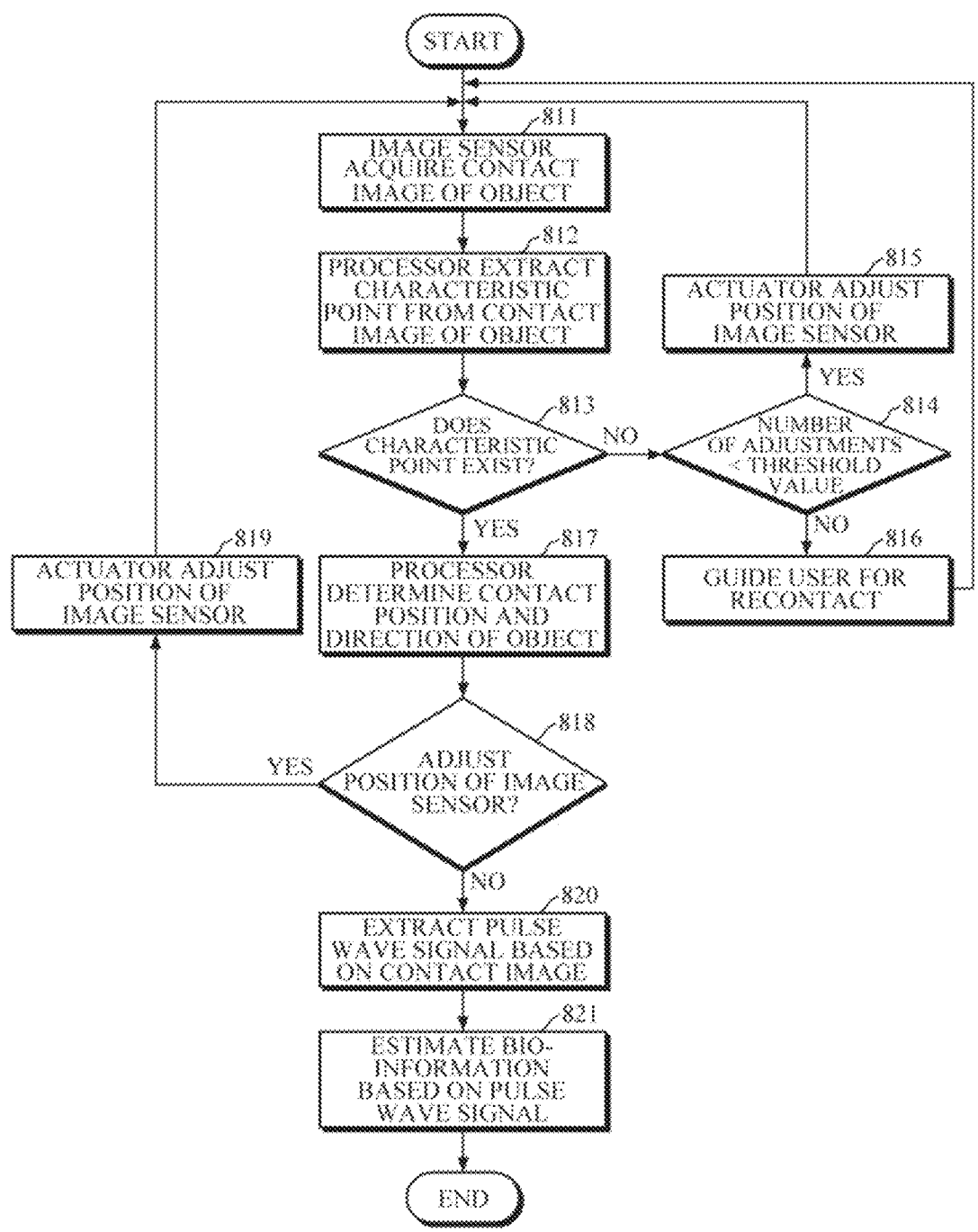
FIG. 8 is a flowchart illustrating a method of estimating bio-information according to still another example embodiment.

FIG. 8 is a flowchart illustrating a method of estimating bio-information according to an example embodiment.

The method of FIG. 8 may correspond to another embodiment of the method performed by the apparatuses 100, 200, and 300 for estimating bio-information according to the embodiments of FIGS. 1 to 3. The method is described in detail above, and hence will be briefly described hereinafter.

In operation 811, when an object is in contact with the image sensor, the image sensor may acquire a contact image of the object, and in operation 812, the processor may extract a characteristic point from the acquired contact image of the object. In this case, the characteristic point is a reference point within a desired measurement area of the object and may include, for example, a center point of a fingerprint or a position of a predetermined blood vessel within the measurement area.

When the characteristic point is not extracted (i.e., does not exist) in operation 812 (operation 813—No), in operation 814, it is determined whether the number of times that the position of the image sensor is adjusted for extracting a characteristic point is less than a threshold value.

When the number of times that the position of the image sensor is adjusted is less than the threshold value, in operation 815, the position of the image sensor may be arbitrarily adjusted by driving the actuator. When the number of times that the position of the image sensor is adjusted is greater than or equal to the threshold value, in operation 816, the user may be guided for recontact.

When the characteristic point is extracted (i.e., does exist) in operation 812 (operation 813—Yes), in operation 817, the contact position and direction of the object may be determined based on the extracted characteristic point. In this case, the contact position and direction may be determined based on the extracted characteristic point and the center point of the FOV of the image sensor.

In operation 818, based on the determined contact position and direction, it may be determined whether the position of the image sensor is to be adjusted.

When the position of the image sensor is to be adjusted, in operation 819, the position of the image sensor may be adjusted by driving the actuator.

When the position of the image sensor is not to be adjusted, in operation 820, a pulse wave signal may be extracted based on the contact image, and in operation 821, bio-information may be estimated based on the extracted pulse wave signal.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information, the apparatus comprising:

an image sensor configured to acquire a first contact image of an object, based on the object being in contact with the image sensor;
an actuator; and
a processor configured to:
  determine a contact position and a direction of the object, based on the acquired first contact image;
  control the actuator to adjust a position of the image sensor, based on the determined contact position and the determined direction of the object so that a field of view (FOV) of the image sensor moves to a predefined measurement area on the object;
  control the image sensor to acquire a second contact image of the object, based on the position of the image sensor being adjusted,
  extract a pulse wave signal based on a pixel intensity of the second contact image; and
  estimate the bio-information based on the pulse wave signal.

2. The apparatus of claim 1, wherein the processor is further configured to:
  extract a characteristic point of the object, from the acquired first contact image; and
  determine the contact position and the direction, based on the extracted characteristic point.

3. The apparatus of claim 2, wherein the characteristic point of the object comprises a fingerprint center point of a finger.

4. The apparatus of claim 2, wherein the processor is further configured to:
  determine whether the extracted characteristic point exists in the first contact image; and
  based on the extracted characteristic point being determined to not exist in the first contact image, guide a user to bring the object into contact with the image sensor.

5. The apparatus of claim 2, wherein the processor is further configured to:
  determine whether the extracted characteristic point exists in the first contact image; and
  based on the extracted characteristic point being determined to not exist in the first contact image, repeat a predetermined number of times of controlling the actuator to adjust the position of the image sensor to an arbitrary position and then extracting the characteristic point, from the acquired first contact image acquired after the position of the image sensor is adjusted.

6. The apparatus of claim 2, wherein the processor is further configured to:
  determine whether the extracted characteristic point exists in the first contact image; and
  based on the extracted characteristic point being determined to not exist in the first contact image, estimate a position of the characteristic point by comparing a reference contact image and the acquired first contact image.

7. The apparatus of claim 1, wherein the processor is further configured to:
  determine a displacement of the image sensor, based on the determined contact position and the determined direction; and
  control the actuator to adjust the position of the image sensor, based on the determined displacement.

8. The apparatus of claim 1, wherein the processor is further configured to:
  generate an oscillogram, based on the pulse wave signal and a contact pressure of the object; and estimate the bio-information, based on the generated oscillogram.

9. The apparatus of claim 8, further comprising a force/pressure sensor configured to measure a contact force or the contact pressure that is applied between the object and the image sensor, based on the object in contact with the image sensor changing a force.

10. The apparatus of claim 8, wherein the processor is further configured to acquire the contact pressure, based on the pixel intensity of the acquired second contact image and using a predefined contact pressure conversion equation.

11. The apparatus of claim 1, wherein the bio-information comprises any one or any combination of a blood pressure, a vascular age, an arterial stiffness, an aortic pressure waveform, a blood vessel elasticity, a stress index, and a degree of fatigue.

12. A method of estimating bio-information, the method comprising:
    acquiring, by an image sensor, a first contact image of an object, based on the object being in contact with the image sensor;
    determining, by a processor, a contact position and a direction of the object, based on the acquired first contact image;
    controlling, by the processor, an actuator to adjust a position of the image sensor, based on the determined contact position and the determined direction of the object so that a field of view (FOV) of the image sensor moves to a predefined measurement area on the object;
    acquiring a second contact image of the object based on the position of the image sensor being adjusted;
    extracting a pulse wave signal based on a pixel intensity of the second contact image; and
    estimating bio-information based on the pulse wave signal.

13. The method of claim 12, wherein the determining of the contact position and the direction comprises:
    extracting a characteristic point of the object, from the acquired first contact image; and
    determining the contact position and the direction, based on the extracted characteristic point.

14. The method of claim 13, further comprising:
    determining whether the extracted characteristic point exists in the first contact image; and
    based on the extracted characteristic point being determined to not exist in the first contact image, guiding a user to bring the object into contact with the image sensor.

15. The method of claim 13, further comprising:
    determining whether the extracted characteristic point exists in the first contact image; and
    based on the extracted characteristic point being determined to not exist in the first contact image, repeating a predetermined number of times of controlling the actuator to adjust the position of the image sensor to an arbitrary position and then extracting the characteristic point, from the acquired first contact image acquired after the position of the image sensor is adjusted.

16. The method of claim 13, further comprising:
    determining whether the extracted characteristic point exists in the first contact image; and
    based on the extracted characteristic point being determined to not exist in the first contact image, estimating a position of the characteristic point by comparing a reference contact image and the acquired first contact image.

17. The method of claim 12, wherein the controlling of the actuator comprises:
    determining a displacement of the image sensor, based on the determined contact position and the determined direction; and
    controlling the actuator to adjust the position of the image sensor, based on the determined displacement.

18. The method of claim 12, wherein the estimating of the bio-information comprises:
    generating an oscillogram, based on the pulse wave signal and a contact pressure of the object; and
    estimating the bio-information, based on the generated oscillogram.

* * * * *